United States Patent [19]
Zarka

[11] 3,969,928
[45] July 20, 1976

[54] NON-DESTRUCTIVE TESTING METHOD FOR DETERMINING A BODY'S MECHANICAL PROPERTIES AND STRESSES

[75] Inventor: Joseph Zarka, Bagneux, France

[73] Assignees: SKF Compagnie d'Applications Mecaniques; Anvar, Agence Nationale de Valorisation de la Recherche, both of France

[22] Filed: June 25, 1974

[21] Appl. No.: 483,022

[30]  Foreign Application Priority Data
June 26, 1973  France .............................. 73.23319
Feb. 21, 1974  France .............................. 74.5884

[52] U.S. Cl. ................................ 73/88 R; 73/81; 73/94
[51] Int. Cl.² ......................................... G01N 3/08
[58] Field of Search ................... 73/88 R, 81, 94, 78

[56] References Cited
UNITED STATES PATENTS

| | | | |
|---|---|---|---|
| 1,312,805 | 8/1919 | Palmgren | 73/88 R |
| 1,781,002 | 11/1930 | Pelterie | 73/81 |
| 1,825,387 | 9/1931 | Pelterie | 73/94 |
| 2,377,590 | 6/1945 | Talalay | 73/89 |
| 3,106,837 | 10/1963 | Plumb et al. | 73/88 R X |
| 3,763,697 | 10/1973 | Sturm | 73/88 R |

*Primary Examiner*—Charles A. Ruehl
*Attorney, Agent, or Firm*—Stevens, Davis, Miller & Mosher

[57] ABSTRACT

The mechanical properties within a part are determined as a function of depth in a non-destructive manner by punching the body with a series of punches having different radii of curvature. Using a plastic criterion with the data obtained the elastic limit of the body as a function of depth is determined as well as the residual self-stresses that exist in the part.

18 Claims, 4 Drawing Figures

NON-DESTRUCTIVE TESTING METHOD FOR DETERMINING A BODY'S MECHANICAL PROPERTIES AND STRESSES

BACKGROUND OF THE INVENTION

The present invention relates to a method of determining the prevailing field of elastic or residual stresses. The invention makes use of punching the body in an elastic manner by means of large radii spheres or balls and applies Hertz' theory of elastic contact of two solids.

With regard to the first application of determining mechanical properties, the present invention relates to a nondestructive testing method for determining the elastic limit of a body as a function of depth. The invention is of particular significance for metal parts that have been subjected to a surface treatment such as a thermal treatment in order to increase the surface hardness.

DESCRIPTION OF THE PRIOR ART

The conventional testing methods previously used for determining the depth of surface treatments for metallic parts or bodies frequently has been the destructive kind for parts which have small dimensions. A portion is selected and cut out in order to determine the effective depth of the hard surface layer that was obtained from the surface treatment.

With regard to larger parts which are frequently manufactured in small lots or even singly, the accuracy relating to the effective depth of the surface treatment is of particular significance and is quite difficult to obtain. Hence there will be more rejects than for smaller parts, and more accurate determination of the properties of the part as a function of depth becomes correspondingly more important. Further, the destructive tests on large parts of single manufacture obviously are economically undesirable.

These being the conditions, it is known how to determine the hardness of such large parts by means of conventional hardness tests, the result then being compared with those from parts of known hardness and made of an identical material. Starting from such a hardness measurement, one may then compute by means of fairly complex calculations the value of the elastic limit as a function of depth, this value being required for ascertaining the part's mechanical properties. The relative complexity of computations is due to their dealing with the plastic domain.

As regards the second application, the present invention relates to a non-destructive testing method for determining the residual stresses, also called "self-stresses" that prevail in a part that may only slightly be work-hardened such as steel. It is known that the residual stresses must be known if a given structure is to be used with maximum or optimum efficiency. The sum of the operational and residual self stresses must remain below the selected criterion of strength such as the plastic limit, the fragile fracture, fatigue, etc.

It is known that mechanical parts frequently will be subject to residual or self-stresses that may have been caused during the heat treatment, during shaping or during machining. Conventional methods that allow measuring of the self-stresses most often are destructive or at least injurious to the part. Quite frequently, indeed, one must resort to a cut-out in order to ascertain the stress tensor.

It has also been suggested to make use of non-destructive tests, for instance by irradiating the parts with x-rays, or by punching them with little spherical or pyramidal punches, or by exposing them to acoustic waves. However, because of the very shallow penetration of x-rays and of the methods utilizing punching or acoustic waves, the results not only are quite difficult to obtain, but furthermore will always be incomplete.

SUMMARY OF THE INVENTION

The object of the present invention is to remedy these drawbacks and to provide a testing method of non-destructive nature which is particularly suitable to large parts for which one desires to know the elastic limit as a function of depth.

Another object of the present invention is a direct method for determining the elastic limit of a part as a function of depth, the load applied to the part in said method being such that the elastic limit will never be exceeded.

Another object of the present invention is a method determining the elastic stresses prevailing in a loaded solid or of the stresses of a non-loaded part by applying Hertz' theory of the elastic contact law for two solids.

Another object of the present invention is a method for determining the field of the residual stresses prevailing at the surface of a loaded solid or in a loaded thin plate.

Another object of the present invention is a non-destructive method for determining the field of the residual stresses inside the solid in certain cases.

Lastly, another object of the present invention is a wholly non-destructive method for the determination of the residual stresses which leaves no trace whatever on the part's surface.

According to the method of the present invention for determining the elastic limit, the part which is to have its elastic limit measured as a function of depth is subjected at its surface to the increasing pressure exerted by a punch. The surface of the punch in contact with the part will preferably be spherical and will have a first radius of curvature.

For each punch pressure applied, the deformation of the part's surface in the vicinity of the punch will be recorded. As long as the deformation everywhere remains elastic, the stress everywhere will be proportional to the applied force. Hence the deformation also will be proportional to the applied force. Progressively increasing the applied force will allow the determination of the precise value of the applied force for which the deformation ceases to be proportional to the applied force. The corresponding force, $F_{el}$, therefore will be that force for which the deformation ceases to be elastic for the punch being used having the given first radius of curvature. Pressure is then removed from the punch so that the part's surface deformation is reversible, thereby assuring the nondestructive nature of the test.

A curve relating the main stresses as a function of depth will be drawn for such a value of applied force being equal to $F_{el}$, taking into account the punch's radius of curvature. Such a relation, in particular, may be that defined by a plasticity criterion such as Tresca's or von Mises'.

One then undertakes successive and identical operations by means of a punch similar to the previous one but with a radius of curvature different from the first's, so that a new elastic force $F_{el}$, and a new curve as a function of depth may be obtained in a similar manner for the punch having the different second radius of curvature.

This operation is repeated by means of a given number of punches with various radii of curvature, whereby a family of curves will be obtained, each representing the relation between the main stresses as a function of depth for each punch radius of curvature parameter. The relation between the main stresses shown on the above mentioned curves being defined by a plasticity criterion, the elastic limit as a function of depth for each given punch radius will be represented by a point on one of these curves. One next traces an envelope-curve for these previous curves. This envelope-curve provides the sought-for variations of the part's elastic limit as function of depth.

The values of the different punch radii of curvature preferably will be so selected that the maxima of the curves representing the relation between the main stresses will be located at the depths where it is desired to study the part's elastic limit.

In another embodiment for determining the elastic stresses of a loaded part only slightly work-hardenable such as steel or of the residual stresses of a non-loaded part of a material only slightly work-hardenable the same instruments will be used. The method of the invention comprises the following steps. First a compression force will be applied by means of a punch at a given point of the part so as to superpose an additional field of stress to the residual ones, and in such manner that the proportionality limit will just be reached near the part's surface. Then a plasticity criterion will be applied to the total field obtained in order to deduce a relation between the residual stresses.

In some special cases, the relation which is obtained already provides significant information about the field of the residual stresses. The complete determination of these residual stresses is obtained by adding the relation determined to the ordinary equilibrium equations and to the part's boundary conditions which must be satisfied by these residual stresses.

A preferred embodiment to ascertain variations in the part's residual stresses as a function of depth comprises applying several different compressive forces to the same point of the part in a successive manner by means of punches with varying radii of curvature so that each time the proportionality limit will just be reached at different points in the part. Then each time a plasticity criterion is applied to the total stress field so obtained and a relation between the desired residual stresses as function of depth can be determined as previously described.

The punches may be hemispherical, in which case the additional field introduced will be one of a symmetry of revolution. In another preferred embodiment of the invention, a cylindrical or ellipsoidal punch is used, and three different compression forces are applied successively to the same point in the part by the same cylindrical or ellipsoidal punch, which each time was made to rotate about itself by a given angle so as to just reach each time the proportionality limit in the vicinity of the part's surface. Triple application of a plasticity criterion to the total field thus obtained allows deducing three relations to determine the residual stresses being sought.

Finally, a further embodiment of the present method involves successively applying three different compression forces by means of a hemispherical, ellipsoidal or cylindrical punch after such a punch has been rotated once about its own axis by a given angle.

The method of the present invention preferably can be implemented by means of instrumentation especially adapted to the purpose which provides the user immediately with the information being sought. Such instrumentation preferably will comprise means for applying a variable compression to the part being tested by means of hemispherical, ellipsoidal or cylindrical interchangeable punches with different radii of curvature; means for measuring the instantaneous compression force being applied; means connected to extensometric or strain gauges located on the part in the vicinity of the compression point for the purpose of instantaneous measurement of the part's deformations; means for detecting the proportionality limit and for stopping application of the compression force while simultaneously ascertaining the limit value of said force; and means for automatically analyzing the measurement results and for providing the sought-for data as function of mathematical criteria and equations.

The present invention will be better understood in conjunction with the description of two particular embodiments illustratively rendered below and illustrated by the attached drawings, without thereby implying any kind of limitation whatever.

DESCRIPTION OF THE PREFERRED EMBODIMENTS

Figure 1:
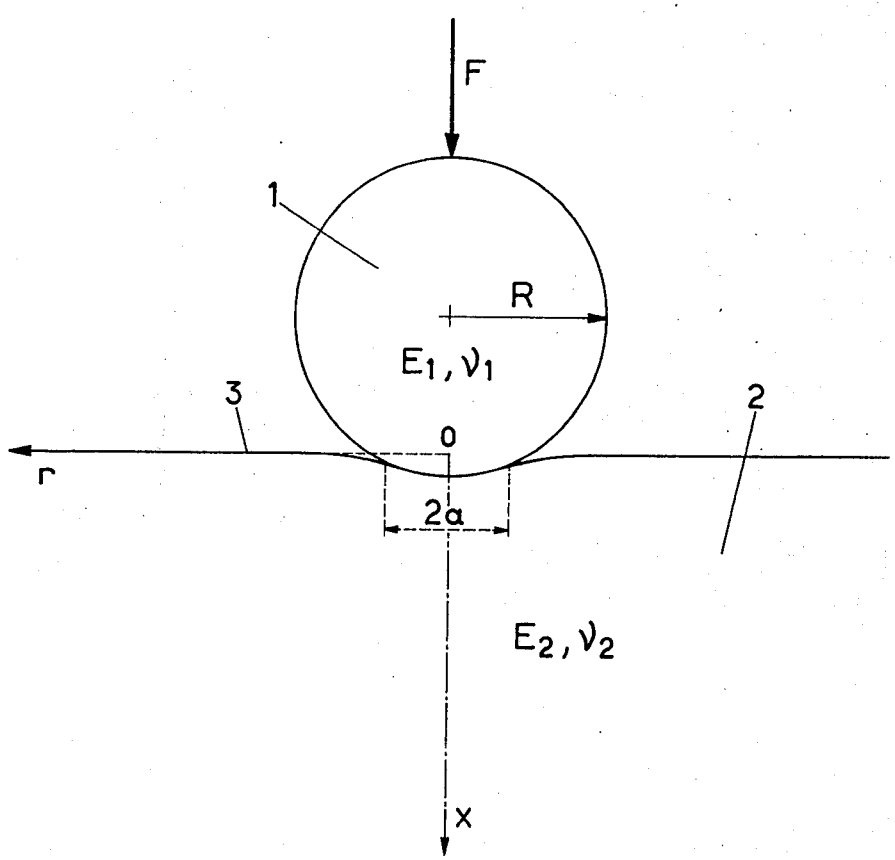
FIG. 1 shows in diagrammatic form a spherical punch acting on the plane surface of a part to be tested and having been subjected to surface treatment.

FIG. 1 shows schematically a ball-shaped punch 1 of radius R and made of a material with an elasticity modulus $E_1$ and a Poisson ratio $\nu_1$.

Ball 1 is applied with a force F against surface 3 of part 2 which has an elasticity modulus $E_2$ and a Poisson ratio $\nu_2$. It should be noted that $E_2$ and $\nu_2$ are invariant, as shown by experience.

For the sake of simplicity, surface 2 is shown as a plane in FIG. 1. It should be understood that the invention also applies to convex and concave surfaces.

It is known that elastic punching of a surface considered to be semi-infinite having an elastic modulus $E_2$ and a Poisson ratio $\nu_2$ by means of a ball of radius R having an elastic modulus $E_1$ and a Poisson ratio $\nu_1$ will be given by the Hertz formulas which provide in particular the radius $a$ of the contact zone between ball and surface. It is seen from FIG. 1 that the ball of radius R will penetrate under the action force F, the radius $a$ of the contact zone being given by the formula:

$$a = \sqrt[3]{\frac{3FR}{4E}} \quad (1)$$

$$\text{or:} \quad \frac{1}{E} = \frac{(1-\nu_1^2)}{E_1} + \frac{(1-\nu_2^2)}{E_2} \quad (2)$$

It is also known that under these conditions, the maximum normal pressure of the ball is given by:

$$\sigma 0 = \frac{3F}{2\pi a^2} \qquad (3)$$

In the cylindrical coordinates defined by FIG. 1 by axes $O_x$ and $O_r$, the stress tensor for the points located on the part's $O_x$ axis reduces to $\sigma_{xx}$, $\sigma_{rr}$ and $\sigma_{\theta\theta}$ which are a function of $\sigma_0$ and depth $x$. The Tresca criterion for plasticity may be used for the present invention; it is given by:

$$D(x) = |\sigma_{xx} - \sigma_{\theta\theta}|\ /2 = K(x) \qquad (4)$$

where K is the material elastic limit at the point under consideration. It is understood that other plasticity criteria also may be used in order to determine a relation such as (4) between the main stresses.

In order to measure the part's surface deformation, one may use for instance tensiometric or strain gauges placed in the vicinity of the contact zone. So long as the deformations remain elastic, the signal displayed by the gauges regardless of their position or orientation will be directly proportional to the applied force F. It is an easy matter therefore to trace the deformation curve as a function of the applied force and to detect the instant the signal no longer will be proportional to the applied force, so that the $F_{el}$ may be determined which corresponds to the elastic limit reached at a point along the $O_x$ axis.

Starting from this value of $F_{el}$ and from the known magnitude of the ball's radius R, the value of $a$ may be determined provided it be assumed that the modulus of elasticity $E_2$ and the Poisson ratio $\nu_2$ will not vary with the part's depth. Indeed it is known that these values are invariant, even when the part is surface-treated. Knowing the value of $a$, the maximum normal pressure $\sigma_{0el}$ may be determined for $F = F_{el}$. Next one determines the stresses $\sigma_{xx}$ and $\sigma_{\theta\theta}$ for all points of the $O_x$ axis and one may then trace the curve of D as a function of $x$.

Figure 2:
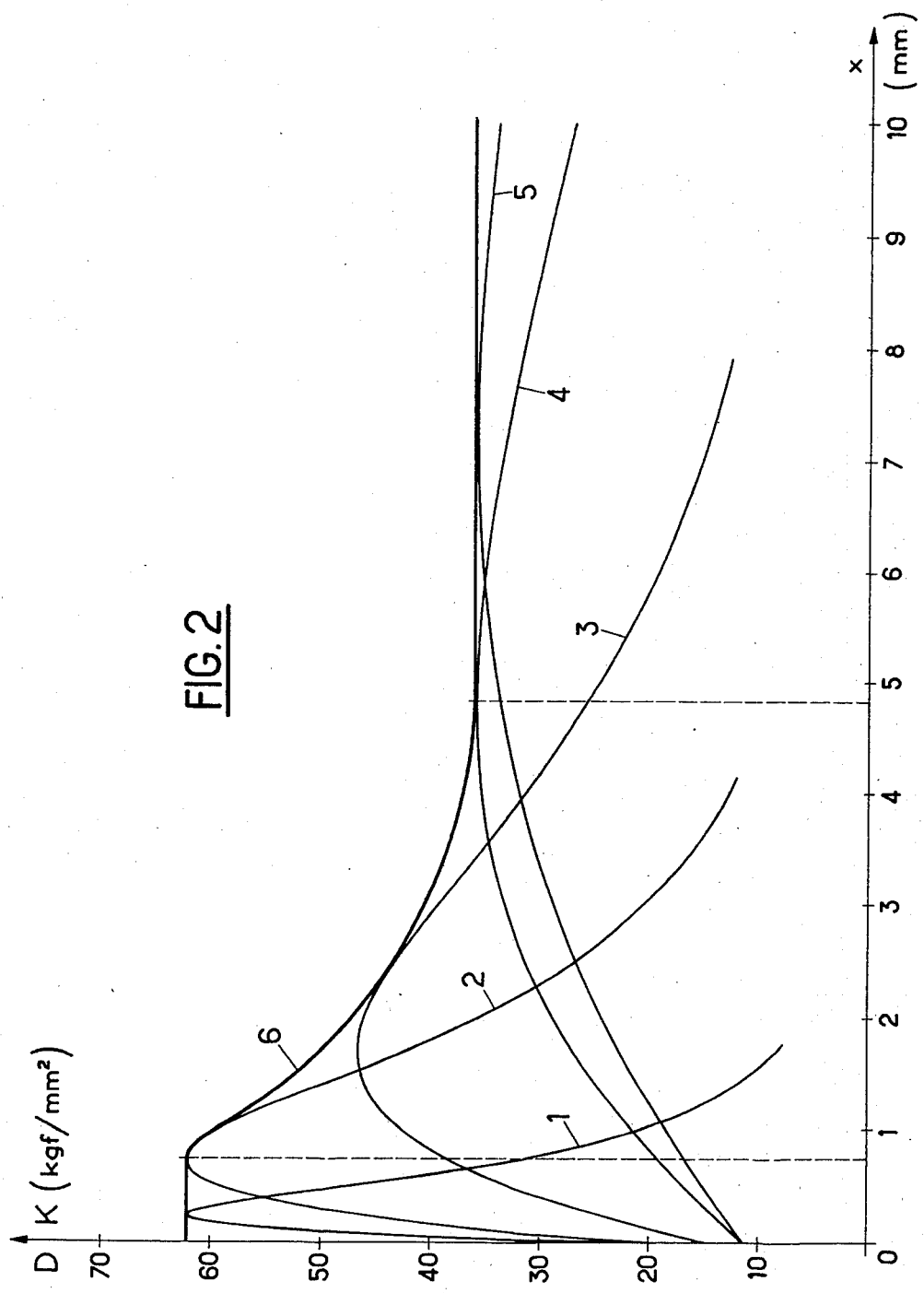
FIG. 2 shows the family of curves from a measurement by means of different radii of curvature punches.

Given the first measurement by means of a ball of radius $R_1$, one then obtains curve 1 shown on FIG. 2. It will be noted that this curve has a maximum inside the part.

Repeating the measurement by means of a ball of radius $R_2$ larger than $R_1$, one obtains similarly a second curve referenced by 2 in FIG. 2, which also shows a maximum shifting towards the inside of the part. It is seen therefore that by changing the ball's radius R, one may shift inward the location of the part's plastic point.

If the part were homogeneously plastic, i.e., if the elastic limit were the same everywhere along axis $O_x$, one would obtain a family of curves of which the maxima would be located on a straight horizontal line.

But in the present instance, where the part is provided with a surface layer of different hardness, the family of curves obtained will be as shown in FIG. 2 by curves 1 through 5, corresponding to an increasing ball radii.

Curves 1 through 5 represent a plasticity function as will follow from the Tresca criterion used in the present example. The elastic limit as a function of depth $x$ is a point necessarily located for each value of radius R of the ball on one of those curves. This point being unique, curve-envelope 6 of the family of curves 5 necessarily represents curve $K(x)$, i.e., the part's elastic limit as function of depth.

As regards the example shown in FIG. 2, it will be noted that the part is endowed with a zone with an elastic limit of about 61 kgf/mm² for a depth of about 1 mm: the elastic limit decreases from that value to about 37 kgf/mm² at a depth of about 5 mm. It is seen therefore that at that depth, the heat treatment no longer is effective.

The radii R of the various balls will be advantageously selected in such manner that the envelope will effectively provide the elastic limit in the depth zone to be tested.

In practice, the points of tangency being in the vicinity of the respective maxima of the $D(x)$ curves, the radii R will be so selected that said maxima, which occurs at a depth approximately equal to $a/2$ if $\nu_2 = 0.3$ will be located in the depth zone under study.

In the example described, this zone exists from about 0.3 to 7 mm in depth.

It is understood that the elastic limit also might have been restricted to a zone lying for instance between 3 and 5 mm in depth.

In practice, typical hardening depths are of the order of a few milimeters. The ball radii then must be of the order of 1,000 mm. Advantageously punches may be used with spherical caps of very small sizes having radii of curvature for example, staggered from 60 to 1,200 mm. Preferably the punches are made of carbon steel with a very high elastic limit and a very high modulus of elasticity.

Figure 3:
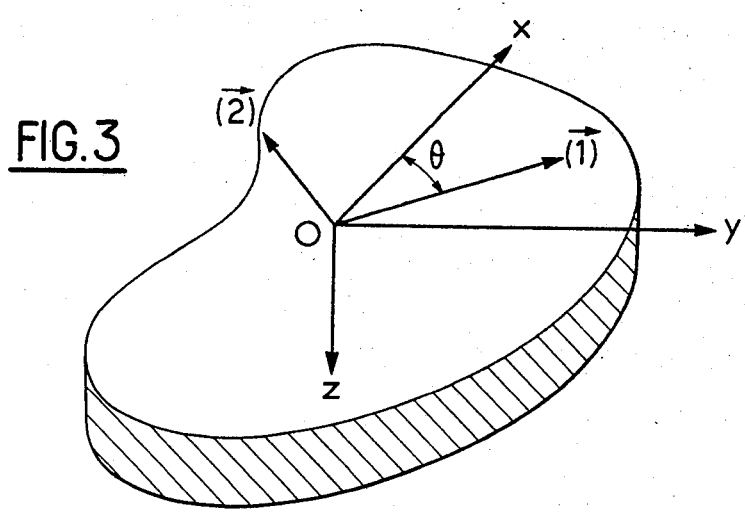
FIG. 3 shows diagrammatically an element of a plate of which one wishes to know the residual stresses.
Figure 4:
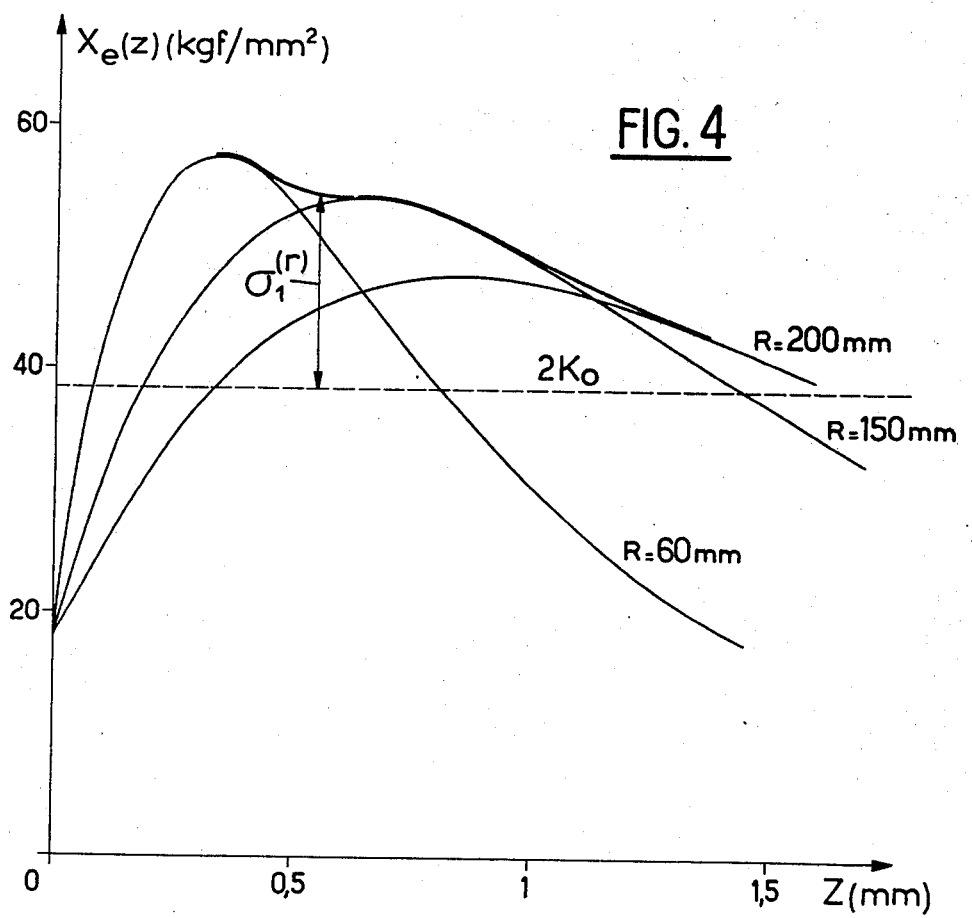
FIG. 4 is a graph which permits the determination of the largest of the main residual stresses prevailing in the plate of FIG. 3.

Considering FIGS. 3 and 4, the part shown in FIG. 3 is a thin plate or shell of an elastic material about 20 mm thick which is only slightly work-hardenable. If one wishes to known the prevailing residual stresses, it is reasonable to assume that the field of self-stresses is a constant field of plane stresses within the shell thickness. If the residual stress field is referenced with respect to the main directions 1 and 2 and if the angle $\theta$ is denoted by the angle $(O_x, 1)$ the residual stress tensor may be written as:

$$\underset{(x,Y)}{\overset{(r)}{\Sigma}} = \begin{pmatrix} \sigma_1^{(r)} & 0 & 0 \\ 0 & \sigma_2^{(r)} & 0 \\ 0 & 0 & 0 \end{pmatrix} \qquad (5)$$

where the three unknown functions to be determined are $\theta(x, Y)$, $\sigma_1^{(r)}(x, Y)$ and $\sigma_2^{(r)}(x, Y)$.

By elastically punching in a direction normal to the plate or shell by means of a ball, a compressing force will be exerted, which superposes a Hertz stress tensor $\Sigma^{(H)}$ known from Hertz' formulas.

The stress tensor reduces to expression (6) in the reference frame of the main directions and on the punching axis as follows:

$$\underset{(Z)}{\overset{(H)}{\Sigma}} = \begin{pmatrix} \sigma_1^{(H)} & 0 & 0 \\ 0 & \sigma_1^{(H)} & 0 \\ 0 & 0 & \sigma_3^{(H)} \end{pmatrix} \qquad (6)$$

Stresses $\sigma_1^{(H)}$ and $\sigma_3^{(H)}$ may be computed by using Hertz' formulas as a function of the geometry of the respective ball and shell materials and of the applied compressive force F. Thus the stresses $\sigma_1^{(H)}$ and $\sigma_3^{(H)}$ may be expressed as functions of $\sigma_0$, the maximum normal pressure below the ball, and in the same manner as before:

$$\sigma_0 = \frac{3F}{2\pi a^2} \qquad (3)$$

Further, there will be a pure shear directly proportional to the applied force F on the surface of the shell and beyond the contact zone. An extensometer or strain gauge glued to the surface of the shell in the vicinity of the punch point of action allowed accurate determination of the instant beyond which the deformations no longer will be proportional to the stresses, that is, it will show the force $F_e$ for which the proportionality limit will have been reached when a single shell point has been plasticized.

The above illustrates that the method of the invention does not require exceeding the proportionality limit and thus is perfectly non-destructive.

If it is assumed the material obeys Tresca's plasticity criterion, then when this criterion is applied to the total stress field, $$\Sigma = \Sigma^{(r)} + \Sigma^{(II)} \qquad (7)$$

one obtains:

$$\sigma_1^{(r)}(x,y) = 2k_o - Xe\left(\frac{a}{2}\right) \qquad (8)$$

where $k_o$ is the constant in Tresca's criterion;

$$X(z) = \sigma_1^{(II)} - \sigma_3^{(II)}$$

where the index $e$ shows that the applied force is $F_e$ for which only a single point has been plasticized; and where $a$, the radius of the contact surface of ball and shell, may be found from Hertz' formulas.

It is seen therefore that the above formula determines the largest of the residual main stresses $\sigma_1^{(r)}$ at all points of the shell.

Use of another plasticity criterion, such as von Mises' would allow determining in similar manner a relation between the main stresses $\sigma_1^{(r)}$ and $\sigma_2^{(r)}$.

The relation between these main stresses as provided by the invention allows complete determination of the self-stress field. The self-stress field, which is in equilibrium with the zero forces along the shell contour, must satisfy not only two equilibrium equations of a two-dimensional stress state, but also the boundary conditions at the shell periphery. Introduction of the relation between the main stresses obtained from punching allows complete determination of the values and orientation of the residual stresses.

As shown by the above example, the method of the present invention allows obtaining instantaneously as a result of a single punching an estimate of the residual stress field prevailing at the surface of an elastic solid which is only slightly cold workable.

The method also allows completely determining this field by integrating a convention system of partial differential equations.

In a second example for the implementation of the invention's method, several punchings are resorted to by means of balls with different radii. One may in this instance obtain at once the variation of the largest of the main stresses as a function of depth, assuming that the stress field remains plane and that a plasticity criterion such as Tresca's indeed is found to apply.

Values for $X_e(z)$ corresponding to different applied forces $F_e$ are obtained for balls of different radii. FIG. 4 shows different curves representing the variation of $X_e$ as function of depth and for various values of radii R of the punching balls such as 60,150 and 200 mm.

The distance from the horizontal straight line $2k_o$ and the envelope-curve represents the value of $\sigma_1^{(r)}$ which thus is given as function of depth $z$ by a formula similar to expression (8):

$$\sigma_1^{(r)} = 2k_o - X_e(zc)$$

where $zc$ is the depth of the point where the proportionality limit is just reached.

It will be noted from the last example that the method of the present invention allows determining the largest residual stresses, $\sigma_1^{(r)}$, as a function of the part's depth.

A third example of implementing the invention is the use of an ellipsoidal punch. In the previous examples, the stress field caused by the ball assumed a symmetry of revolution, and there was no effect from the angle $\theta$ between the axis $O_x$ and direction 1. In the present instance, on the contrary, one wishes to generate an additional and asymmetrical stress field by means of an ellipsoidal or cylindrical punch. By acting with this punch as previously, i.e., by rotating it each time about the $O_z$ axis, one may by means of three successive measurements of the elastic limit force $F_e$ determine the three unknowns of the residual stress tensor, namely $\theta$, $\sigma_1^{(r)}$ and $\sigma_2^{(r)}$.

The reference frame being defind by the angle subtended with respect to a fixed direction, the angular position of the ellipsoidal or cylindrical punch is then modified i.e. one changes the value of angle $\alpha$. The main or principal directions of the residual stress tensor $\Sigma(r)$ are unknown but obviously remain fixed in the part when angle $\alpha$ is changed, and the residual stress tensor may be expressed as a function of the angle $\theta$ between the $O_x$ axis and the main or principal direction.

By reasoning similar to that above, it will follow that the use of a plasticity criterion will allow establishing a relation between $\sigma_1^{(r)}$, $\sigma_2^{(r)}$ and $\theta$ for each position of the ellipsoidal or cylindrical punch, that is, for each value of $\alpha$. If one measures again with three different values of the angle $\alpha$, three relations between these three unknowns will be obtained, which allow for the complete determination of these unknowns.

In practice, it will be preferable to vary the angle each time by 45°, causing a variation of 90° in $\theta$, whereby computations will be simplified.

Although the examples and embodiments of the invention described above were applied to the case of a plane plate or shell for the sake of simplicity, the expert will easily understand that the present method for determining the residual stresses can be applied to other parts, for instance to circular section cylinders, to spheres or even to parts of arbitrary shape, provided the part's material be only slightly cold workable. In practice, one may also implement the present method by performing a first measurement by means of a spherical punch, since this first measurement already will provide a significant indication of the residual stress field, as explained above. This first measurement may be followed by two measurements carried out successively by means of an ellipsoidal or cylindrical punch following rotation of the latter about its axis and by a given angle, for instance 90°, in order to simplify computations. These three measurements will be preformed as described above and will allow determining the residual stress field by means of these three relationships.

The term "residual" stress has been continuously used in the present description. The expert will easily comprehend that the invention will apply similarly to measuring the elastic stresses prevailing in a loaded solid.

Thus, the present invention allows extremely rapid and accurate determination of the elastic limit of a material as a function of depth and of the residual or elastic stresses present in the part. Because the deformations caused by the method of the present invention always remain within the elastic domain, the test being performed will be non-destructive and if desired, one may deduce the hardness of the material as a function of depth from the elastic limit thus obtained since the computations involved are hardly complex as one never deals with the plastic range. The present invention may be advantageously applied to measuring the mechanical properties of metal parts of large sizes, and quite particularly those parts which were subject to surface treatment such as hardening, cementation or cold working for the purpose of increasing the part's surface hardness.

What is claimed is:

1. A non-destructive testing method for determining the elastic limit of a body or part as a function of depth suitable for a part having been subjected to surface treatment comprising:
   a. subjecting the surface of said part to an increasing pressure exerted by a series of punches, each punch having a contact surface with a different radii of curvature;
   b. measuring the deformation in the vicinity of the punch of the surface of said part for each punch pressure;
   c. measuring the force ($F_{e1}$) at which the deformation for each punch ceases to be elastic;
   d. removing the pressure applied to each punch in order that the surface deformation to the part is reversible;
   e. constructing a curve for each punch from the force ($F_{e1}$) data representing the relation between the main stresses as a function of depth; and
   f. constructing an envelope-curve over each of said curves in step (e) whereby said envelope-curve represents the elastic limit of the part as a function of the depth.

2. The method of claim 1 wherein the elastic limit at given depths is determined by selecting the values of the radii of curvature of said punches so that the maxima of the curves representing said relation between the stresses are located at said given depths.

3. The method of claim 1, wherein said punches are hemispherically shaped.

4. The method of claim 1, wherein the relation used in constructing said curve for each punch from said force data ($F_{e1}$) is the Tresca plasticity criterion.

5. The method of claim 1, wherein the relation used in constructing said curve for each punch from said force data ($F_{e1}$) is the Von Mises plasticity criterion.

6. A non-destructive testing method for determining in situ by means of a given plasticity criterion unknown elastic or residual stresses to which a part of material having only slight work-hardening properties remains subjected during the testing steps, comprising:
   a. exerting a compression force at one point of said part by means of an exterior punch to deform said part at said point and to super-impose an elastic stress having known characteristics onto said unknown stresses;
   b. increasing said compression force up to the proportionality limit of said part beyond which the deformation of said part in the vicinity of said point is no longer proportional to the total stresses applied to said part;
   c. measuring the force ($F_{e1}$) at which the deformation for said punch ceases to be elastic;
   d. removing the pressure applied to said punch in order that the surface deformation of the part is reversible;
   e. determining from said given plasticity criterion and from said measured force ($F_{e1}$) and said elastic stress having known characteristics a relationship with the unknown elastic or residual stresses; and
   f. determining the unknown elastic or residual stresses from said relationship from given equilibrium equations for said part and from given boundary conditions at the periphery of said part.

7. The method of claim 6, further comprising exerting successively several different compression forces by punches of various radii of curvature at the same point of the part to obtain the proportionality limit in the part for each punch.

8. The method of claim 7, wherein said punches are hemispherical and said method comprises the further steps of constructing a series of curves graphically expressing the total stress field for each punch used, constructing an envelope-curve for said series of curves and applying said given plasticity criterion in conjunction with said envelope-curve to determine the value of the largest residual stress as a function of depth.

9. The method of claim 6, wherein three different compression forces are successively applied with a given punch to the same point of the part after rotating the given punch each time about its own axis by a given angle so that the proportionality limit is just reached each time in the vicinity of the part's surface.

10. The method of claim 9, wherein the punch is made to rotate 45° each time.

11. The method of claim 9, wherein said punch is ellipsoidal in shape.

12. The method of claim 9, wherein said punch is cylindrical in shape.

13. The method of claim 6, wherein three different compression forces are successively exerted at the same point of the part by means of a given punch following rotation of said punch about its axis by a given angle in such a manner that the proportionality limit is just reached each time in the vicinity of the part's surface, and wherein a plasticity criterion is applied three times to the total field obtained in order to deduce three relations for determining the residual stresses.

14. The method of claim 13, wherein said punch is made to rotate once by 90°.

15. The method of claim 14, wherein said punch is ellipsoidal in shape.

16. The method of claim 14, wherein said punch is cylindrical in shape.

17. The method of claim 14, wherein said punch is hemispheric in shape.

18. A non-destructive testing method suitable for a part having been subjected to surface treatment comprising:
   subjecting the surface of said part to an increasing pressure force exerted by a series of punches, each punch having a contact surface with a different radius of curvature;

measuring the pressure force exerted by each punch at which deformation of said part ceases to be elastic; and determining the variations in the elastic limit of said part as a function of depth from said measured pressure force for each of said punches exerting a pressure force on said part.

* * * * *